United States Patent [19]
Cook et al.

[11] Patent Number: 5,804,210
[45] Date of Patent: *Sep. 8, 1998

[54] METHODS OF TREATING ANIMALS TO MAINTAIN OR ENHANCE BONE MINERAL CONTENT AND COMPOSITIONS FOR USE THEREIN

[75] Inventors: Mark E. Cook; Michael W. Pariza, both of Madison, Wis.

[73] Assignee: Wisconsin Alumni Research Foundation, Madison, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 693,577

[22] Filed: Aug. 7, 1996

[51] Int. Cl.$^6$ ...................................................... A61K 9/68
[52] U.S. Cl. .......................... 424/440; 424/442; 424/464; 424/441; 424/451; 424/807; 514/560
[58] Field of Search ..................................... 424/440, 442, 424/464, 441, 451, 722, 602, 607; 514/560

[56] References Cited

U.S. PATENT DOCUMENTS

| | | | |
|---|---|---|---|
| 4,442,125 | 4/1984 | Thiele | 424/318 |
| 5,017,614 | 5/1991 | Pariza et al. | 514/558 |
| 5,070,104 | 12/1991 | Pariza et al. | 514/549 |
| 5,208,356 | 5/1993 | Pariza et al. | 554/79 |
| 5,318,991 | 6/1994 | Horrobin | 514/560 |
| 5,428,072 | 6/1995 | Cook et al. | 514/560 |
| 5,430,066 | 7/1995 | Cook et al. | 514/558 |

OTHER PUBLICATIONS

Y.L. Ha; N.K. Grimm and M.W. Pariza, *Carcinogenesis*, vol. 8, No. 12, pp. 1881–1887 (1987).

Y.L. Ha; N.K. Grimm and M.W. Pariza, J. Agric. Food Chem., vol. 37, No. 1, pp. 75–81 (1987).

S.F. Chin, W. Liu, J.M. Storkson, Y.L. Ha and M.W. Pariza, Journal of Food Composition and Analysis, vol. 5, pp. 185–197 (1992).

INFORM, vol. 7, No. 2 (Feb. 1996), "Conjugated Linoleic Acid Offers Research Promise".

*Primary Examiner*—Thurman K. Page
*Assistant Examiner*—D. Faulkner
*Attorney, Agent, or Firm*—Quarles & Brady

[57] ABSTRACT

A method of treating an animal to maintain or enhance the mineral content of the bones of the animal consists of administering to the animal a safe and effective amount of CLA. Compositions for use in the method are also disclosed.

12 Claims, No Drawings

METHODS OF TREATING ANIMALS TO MAINTAIN OR ENHANCE BONE MINERAL CONTENT AND COMPOSITIONS FOR USE THEREIN

FIELD OF THE INVENTION

The present application generally relates to methods of treating animals, including humans. More particularly, it relates to methods of treating animals to maintain or enhance the mineral content of bone.

BACKGROUND OF THE INVENTION

It is known that many animals, including humans, lose bone minerals as they age or if they are afflicted with certain diseases. Researchers have observed that bone calcium loss or reduction in humans can cause osteoporosis. It also is known that maintaining or enhancing the bone calcium content can be beneficial in treating or preventing osteoporosis.

Most of the known chemical compounds that maintain or increase the bone calcium in the animal are potent biological agents which can have significant side effects.

It would be advantageous to have methods and compositions for maintaining or enhancing the mineral content of skeletal bones in animals without causing significant undesirable side effects.

BRIEF SUMMARY OF THE INVENTION

It is one object of the present invention to disclose a method of maintaining or enhancing the mineral content of skeletal bones in animals.

It is a still further object to disclose novel compositions for use in the methods of the invention.

We have discovered a method of maintaining or enhancing the mineral content of skeletal bones in an animal, including a human, which comprises administering to the animal a safe and effective amount of a conjugated linoleic acid, such as 9,11-octadecadienoic acid and 10,12-octadecadienoic acid, or active derivatives thereof, such as non-toxic salts, active esters, such as triglycerides, and mixtures thereof.

The conjugated linoleic acids, their non-toxic salts, active esters, active isomers, active metabolics, and mixtures thereof are referred to herein as "CLA."

The compositions of the present invention are pharmaceutical compositions which contain CLA in combination with a source of calcium, such as calcium carbonate, and optionally other ingredients.

It will be apparent to those skilled in the art that the forementioned objects and other advantages may be achieved by the practice of the present invention.

DESCRIPTION OF THE PREFERRED EMBODIMENT

In the preferred method of the present invention for maintaining or increasing the mineral content of skeletal bones of an animal, a safe and effective amount of CLA is administered to the animal.

Although CLA can be administered by itself to enhance or maintain bone mineral content, the preferred compositions of the present invention are pharmaceutical compositions which contain safe amounts of CLA and a calcium source, such as calcium carbonate, calcium phosphate or calcium carbonate. The compositions may also contain, without limitation, pharmaceutical diluents and other ingredients including vitamins, such as Vitamin D, and other minerals, such as zinc and magnesium salts. The pharmaceutical composition may be in the form of tablets, capsules or liquids for oral administration. Since CLA is a natural food ingredient and it is relatively non-toxic, the amount of CLA which can be administered is not critical as long as it is enough to be effective.

The practice of the present invention is further illustrated by the examples which follow:

EXAMPLE 1

Day old broiler chicks were fed a conventional corn/soybean meal diet containing either 0.5% corn oil (control) or 0.5% CLA. The chicks were fed the diets for 27 days. The chicks were then sacrificed and the bones were collected, dried, ether extracted and the ash content percentage was determined using a muffle furnace. The results of percent ash of fat-free, dried bone and of bone as collected are shown in Table 1. The body weights and results of bone evaluation are shown in Table 2.

TABLE 1

| Diet | % Moisture | % Fat | % Ash (fresh weight) | % Ash |
|---|---|---|---|---|
| Control | 44.90 ± 0.93 | 3.94 ± 0.44 | 20.46 ± 0.73 | 51.11 ± 1.74 |
| CLA | 46.22 ± 1.05 | 4.18 ± 0.43 | 23.28 ± 1.13 | 56.32 ± 2.10 |

TABLE 2

| Diet | Body Wt | Shank Width mm | Tibia Width mm | Tibia Length cm | TD* Score |
|---|---|---|---|---|---|
| Control | 737.5 ± 31.41 | 8.0 ± 0.42 | 6.07 ± 0.23 | 6.91 ± 0.11 | 1.6 ± 0.31 |
| CLA | 830.9 ± 29.66 | 8.43 ± 0.23 | 5.91 ± 0.20 | 7.09 ± 0.09 | 1.3 ± 0.15 |

*TD = tibial dyschondroplasia. Growth plates of the tibia were examined for abnormal cartilage accumulation and scored 1 if normal, 2 if slightly enlarged, 3 if moderately enlarged, and 4 if severely enlarged.

The results of the experiments demonstrate that the bones of the chicks fed the diet containing CLA have a higher ash and mineral content than the control chicks. Similar results are obtained in humans.

The methods of the present invention may take several embodiments. In one embodiment, the CLA is administered to an animal in a pharmaceutical or veterinary composition containing a safe and effective dose of the CLA. In another embodiment, the animal is fed a food that has been enriched with CLA.

The animal feeds and pharmaceutical preparations for use in the methods of the present invention are those containing the CLA in combination with a conventional animal feed (e.g. poultry feed), human food supplement, or approved pharmaceutical diluent.

Active forms of CLA include the free conjugated linoleic acids, the active isomers of those acids, non-toxic salts thereof, active esters of those acids, such as the triglycerides, methyl and ethyl esters, and other active chemical derivatives thereof, and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products (Y. L. Ha, N. K. Grimm and M. W. Pariza, in J. Agric. Food Chem., Vol. 37, No. 1, pp. 75–81 (1987)).

The free acid forms of the CLA may be prepared by isomerizing linoleic acid. The non-toxic salts of the free CLA acids may be made by reacting the free acids with a non-toxic base. Natural CLA may also be prepared from linoleic acid by the action of W $^{12}$-cis, W $^{11}$-transisomerase from a harmless microorganism such as the Rumen bacterium *Butvrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The free acids are readily converted into a non-toxic salt, such as the sodium, potassium or calcium salts, by reacting chemically equivalent amounts of the free acid with an alkali hydroxide at a PH of about 8 to 9.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The CLA, in addition to being added to an animal's food, can be administered in the form of pharmaceutical or veterinary compositions, such as tablets, capsules, solutions or emulsions to the animal or the humans. The exact amount to be administered, of course, depends upon the form of CLA employed and the route of administration, and the nature of the animal's or human's condition. Generally, the amount employed of CLA employed as a pharmaceutical will range from about one part per million (ppm) to about 10,000 ppm of CLA (calculated as the free acids) in the human's diet. However, the upper limit of the amount to be employed is not critical because CLA is relatively non-toxic. The amounts of CLA (calculated as the free acids) to be added to food as an additive can range from 0.01% to 2.0% or more by weight of the food.

The preferred pharmaceutical compositions of the present invention contain the non-toxic CLA sodium, potassium, or calcium salts in combination with a calcium source and pharmaceutical diluents. When the compositions are intended for oral administration the dosage forms preferably will be a tablet, a wafer, a capsule or a liquid. When the compositions are solutions or suspensions intended for parenteral administration, the preferred diluent will be Sterile Water for Injection U.S.P.

The calcium sources that may be used in the compositions of the present invention include, without limitation, salts, such as calcium carbonate, calcium gluconate and calcium phosphate. Especially preferred is dibasic calcium phosphate.

A representative pharmaceutical tablet has the following formula:

CLA(calculated as free acids) 600 mg

Dibasic Calcium Phosphate, (anhydrous form) 500 mg

Cholecalciferol (133 IU) 3.33 mcg

Microcrystalline cellulose, sodium starch glycolate, corn starch, hydrogenated vegetable oil wax, magnesium stearate and talc added.

The normal daily dosage to increase or maintain proper bone calcium levels is three to thirty tablets per day. The thirty tablets a day is roughly equivalent to the dose of CLA used in Example 1.

A representative chewable pharmaceutical wafer has the following formula:

CLA(calculated as free acids)1000 mg

Cholecalciferol 5 mcg (200 IU)

Dibasic Calcium Phosphate, (anhydrous form)

Added dextrose, sucrose, talc, stearic acid, mineral oil, salt, and natural and artificial flavorings.

The normal daily dosage is two to twenty tablets a day. The twenty tablets a day is roughly equivalent to the amount of CLA used in Example 1.

Because CLA and calcium salts are relatively non-toxic, doses larger than the normal daily dosages of the compositions may be administered if desired.

It will be readily apparent to those skilled in the art that a number of modifications or changes may be made without departing from the spirit and scope of the present invention. Therefore, the invention is only to be limited by the claims.

We claim:

1. A method of maintaining or enhancing the mineral content of bone in an animal, said method comprising administering orally or parenterally to said animal a safe amount of conjugated linoleic acid, said amount being effective to maintain or enhance said mineral content, the conjugated linoleic acid comprising an isomer having a pair of conjugated double bonds, the isomer being selected from a group consisting of cis-9, cis-11-octadecadienoic acid, cis-9, trans-11-octadecadienoic acid, trans-9, cis-11-octadecadienoic acid, trans-9, trans-11-octadecadienoic acid, cis-10, cis-12-octadecadienoic acid, cis-10, trans-12-octadecadienoic acid, trans-10, cis-12-octadecadienoic acid, and trans-10, trans-12-octadecadienoic acid.

2. The method of claim 1 in which the conjugated linoleic acid is a triglyceride of a conjugated linoleic acid.

3. The method of claim 1 in which the conjugated linoleic acid is a sodium salt of a conjugated linoleic acid.

4. The method of claim 1 in which the conjugated linoleic acid is a potassium salt of a conjugated linoleic acid.

5. The method of claim 1 in which the conjugated linoleic acid is a calcium salt of a conjugated linoleic acid.

6. The method of claim 1 in which the conjugated linoleic acid is 9,11-octadecadienoic acid.

7. The method of claim 1 in which the conjugated linoleic acid is 10,12-octadecadienoic acid.

8. A pharmaceutical composition for maintaining and enhancing bone calcium content comprising safe amounts of conjugated linoleic acid and a calcium source, the conjugated linoleic acid comprising a pair of conjugated double bonds, the isomer being selected from a group consisting of cis-9, cis-11-octadecadienoic acid, cis-9, trans-11-octadecadienoic acid, trans-9, cis-11-octadecadienoic acid, trans-9, trans-11-octadecadienoic acid, cis-10, cis-12-octadecadienoic acid, cis-10, trans-12-octadecadienoic acid, trans-10, cis-12-octadecadienoic acid, and trans-10, trans-12-octadecadienoic acid.

9. A pharmaceutical composition of claim 8 in which the calcium source is dibasic calcium phosphate.

10. A pharmaceutical composition of claim 8 in which the calcium source is calcium carbonate.

11. A method of maintaining or enhancing the calcium content of bone in an animal, said method comprising administering orally or parenterally to said animal safe amounts of a calcium source and conjugated linoleic acid, said amounts being effective to maintain or enhance the calcium content of bone in the animal, the conjugated linoleic acid comprising a pair of conjugated double bonds, the isomer being selected from a group consisting of cis-9, cis-11-octadecadienoic acid, cis-9, trans-11-octadecadienoic acid, trans-9, cis-11-octadecadienoic acid, trans-9, trans-11-octadecadienoic acid, cis-10, cis-12-octadecadienoic acid, cis-10, trans-12-octadecadienoic acid, trans-10, cis-12-octadecadienoic acid, and trans-10, trans-12-octadecadienoic acid.

12. The methods of claim 1 in which the conjugated linoleic acid is an active ester of a conjugated linoleic acid.

* * * * *